(12) United States Patent
Hancock et al.

(10) Patent No.: US 10,321,955 B2
(45) Date of Patent: Jun. 18, 2019

(54) ELECTROSURGICAL FORCEPS FOR DELIVERING RF AND/OR MICROWAVE ENERGY INTO BIOLOGICAL TISSUE

(71) Applicant: Creo Medical Limited, Chepstow (GB)

(72) Inventors: Christopher Paul Hancock, Bath (GB); Malcolm White, Chepstow (GB); Sandra May Bernadette Holmes, Stevenage (GB); Brian Saunders, Rickmansworth (GB)

(73) Assignee: Creo Medical Limited, Chepstow (GB)

( * ) Notice: Subject to any disclaimer, the term of this patent is extended or adjusted under 35 U.S.C. 154(b) by 317 days.

(21) Appl. No.: 15/107,291

(22) PCT Filed: Dec. 23, 2014

(86) PCT No.: PCT/GB2014/053834
§ 371 (c)(1),
(2) Date: Jun. 22, 2016

(87) PCT Pub. No.: WO2015/097472
PCT Pub. Date: Jul. 2, 2015

(65) Prior Publication Data
US 2016/0331455 A1   Nov. 17, 2016

(30) Foreign Application Priority Data
Dec. 23, 2013   (GB) .................................. 1322844.0

(51) Int. Cl.
*A61B 18/00* (2006.01)
*A61B 18/14* (2006.01)
*A61B 18/18* (2006.01)

(52) U.S. Cl.
CPC ...... *A61B 18/1815* (2013.01); *A61B 18/1445* (2013.01); *A61B 18/18* (2013.01);
(Continued)

(58) Field of Classification Search
CPC .......... A61B 2018/00994; A61B 18/18; A61B 18/1815; A61B 2018/1823; A61B 2018/1884
See application file for complete search history.

(56) References Cited

U.S. PATENT DOCUMENTS

2010/0249769 A1* 9/2010 Nau, Jr. ................. A61B 18/18
606/33
2012/0143180 A1   6/2012 Lee, Jr. et al.
(Continued)

FOREIGN PATENT DOCUMENTS

CN        101836881 B      7/2011
CN        103142306 A      6/2013
(Continued)

OTHER PUBLICATIONS

International Search Report and Written Opinion issued in PCT/GB2014/053834 dated Apr. 10, 2015.
(Continued)

*Primary Examiner* — Ronald Hupczey, Jr.
*Assistant Examiner* — Bradford C. Blaise
(74) *Attorney, Agent, or Firm* — Arent Fox LLP

(57) ABSTRACT

Electrosurgical forceps in which one or more pairs of non-resonant unbalanced lossy transmission line structures are arranged on the inner surfaces of the jaws of the forceps provide both (i) active and return electrodes for a radiofrequency (RF) signal, and (ii) lossy structures for delivering a microwave signal into biological tissue in conjunction with a mechanical gripping arrangement for applying pressure to material held within the jaws. The location of the pairs of transmission lines on the jaws of the forceps and the selection of the material of the jaws is arranged to ensure that any biological tissue gripped by the jaws become the
(Continued)

propagation medium for the RF signal and the medium into which the microwave signal is lost.

23 Claims, 7 Drawing Sheets

(52) U.S. Cl.
CPC ............... *A61B 2018/00428* (2013.01); *A61B 2018/00595* (2013.01); *A61B 2018/00607* (2013.01); *A61B 2018/00994* (2013.01); *A61B 2018/1823* (2013.01); *A61B 2018/1884* (2013.01)

(56) References Cited

U.S. PATENT DOCUMENTS

| | | |
|---|---|---|
| 2013/0041361 A1 | 2/2013 | Keller |
| 2013/0144284 A1 | 6/2013 | Behnke, II et al. |
| 2013/0190753 A1* | 7/2013 | Garrison ................ A61B 17/29 606/41 |
| 2013/0267943 A1* | 10/2013 | Hancock ............... A61B 18/042 606/33 |
| 2013/0274733 A1 | 10/2013 | Hancock |
| 2013/0289557 A1* | 10/2013 | Hancock ............ A61B 18/1815 606/33 |

FOREIGN PATENT DOCUMENTS

| | | |
|---|---|---|
| EP | 2 392 282 A1 | 12/2011 |
| FR | 2 767 052 A1 | 2/1999 |
| GB | 2487199 A | 7/2012 |
| GB | 2487288 A | 7/2012 |
| GB | 2503673 A | 1/2014 |
| WO | WO 2009/120953 A2 | 10/2009 |
| WO | WO 2015/052502 A1 | 4/2015 |

OTHER PUBLICATIONS

British Search and Examination Report of related British Patent Application No. GB1423101.3 dated May 15, 2015.
British Search Report of related British Patent Application No. GB1322844.0 dated Aug. 1, 2014.
Extended European Search Report issued in European Patent Application No. 18160694.8 dated Aug. 6, 2018.

* cited by examiner

ELECTROSURGICAL FORCEPS FOR DELIVERING RF AND/OR MICROWAVE ENERGY INTO BIOLOGICAL TISSUE

CROSS-REFERENCE TO RELATED APPLICATIONS

This application is a National Stage entry of International Application No. PCT/GB2014/053834, filed Dec. 23, 2014, which claims priority to British Patent Application No. 1322844.0, filed Dec. 23, 2013. The disclosure of the prior applications are hereby incorporated in their entirety by reference.

FIELD OF THE INVENTION

The invention relates to electrosurgical forceps for grasping biological tissue and for delivering microwave energy into the grasped tissue to coagulate or cauterise or seal the tissue and/or RF energy for cutting the tissue. In particular, the forceps may be used to seal and/or cut blood vessels. The invention may be applied to forceps that can be inserted down the instrument channel of an endoscope or a gastroscope, or may be used in laparoscopic surgery or open surgery.

BACKGROUND TO THE INVENTION

Forceps capable of delivering heat energy into grasped biological tissue are known. For example, it is known to deliver radiofrequency (RF) energy from a bipolar electrode arrangement in the jaws of the forceps. The RF energy may be used to seal vessel by thermal denaturation of extracellular matrix proteins within the vessel wall. The heat energy may also cauterise the grasped tissue and facilitate coagulation.

U.S. Pat. No. 6,585,735 describes an endoscopic bipolar forceps in which the jaws of the forceps are arranged to conduct bipolar energy through the tissue held therebetween.

EP 2 233 098 describes microwave forceps for sealing tissue in which the sealing surfaces of the jaws include one or more microwave antennas for radiating microwave energy into tissue grasped between the jaws of the forceps.

SUMMARY OF THE INVENTION

At its most general, the present invention provides an electrosurgical forceps in which one or more pairs of non-resonant unbalanced lossy transmission line structures are arranged on the inner surfaces of the jaws of the forceps provide both (i) active and return electrodes for a radiofrequency (RF) signal, and (ii) lossy structures for delivering a microwave signal into biological tissue in conjunction with a mechanical gripping arrangement for applying pressure to material held within the jaws. The location of the pairs of transmission lines on the jaws of the forceps and the selection of the material of the jaws is arranged to ensure that any biological tissue gripped by the jaws become the propagation medium for the RF signal and the medium into which the microwave signal is lost. The pressure applied by the mechanical gripping arrangement may form a seal with the gripped tissue due to the resilient behaviour of the tissue and/or jaws of the forceps, which can ensure that the energy is delivered controllably into the gripped tissue.

Thus, according to the invention, there is provided an electrosurgical forceps comprising: a pair of jaw elements pivotable relative to each other to open and close a gap therebetween; a pair of elongate conductive elements mounted in the pair of jaw elements adjacent to the gap; and a coaxial cable for conveying radiofrequency (RF) energy and/or microwave energy, wherein the pair of elongate conductive elements are electrically connected to the coaxial cable and arranged to act as both (i) an active electrode and a return electrode for RF energy conveyed by the coaxial cable, and (ii) a lossy transmission line structure for microwave energy conveyed by the coaxial cable. Herein, the term "lossy transmission line structure" may mean a non-uniform unbalanced lossy transmission line for supporting the microwave energy as a travelling wave, the non-uniform unbalanced lossy transmission line being non-resonant for the microwave energy along the travelling wave. The elongate conductive elements may have a proximal end in electrical connection with an inner conductor or an outer conductor of the coaxial cable and a open circuit distal end. This arrangement places fewer restrictions on the electrode configuration than in microwave forceps where the electrode must form a radiating antenna. Consequently, there is more flexibility in the choice of shape of the jaw elements.

Herein the term "non-resonant" may mean that the electrical length of the transmission line (along the microwave energy travelling wave) is set to inhibit multiple reflections of the travelling wave, i.e. to prevent or inhibit the creation of a radiating standing wave. In practice this may mean that the electrical length of the transmission line is substantially different from a multiple of a quarter wavelength of the microwave energy (an odd or even multiple needs to be avoided depending on whether the distal end of the transmission line is an open circuit or a short circuit). It is particularly desirable for the transmission line to be non-resonant when there is biological tissue in the gap, i.e. in contact with the jaw elements. Thus, the electrical length of the transmission line may be set to avoid a multiple of a quarter wavelength of the microwave energy when the transmission line is loaded by the biological tissue in this way. Preferably the distal end of the transmission line is an open circuit, as this may enable the device to operate with radiofrequency (RF) energy as well as microwave energy.

Forming a non-resonant transmission line may prevent the device from radiating. The microwave energy is therefore delivered into tissue through leakage from the transmission line structure. By setting the length of the transmission line with knowledge of the loss level into biological tissue at the frequency of the microwave energy, the electrosurgical forceps of the invention can be arrange to deliver substantially all of the power received at the proximal end of the transmission line in a single transit of the travelling wave along the transmission line.

In other words, the geometry of the transmission line is selected, e.g. on the basis of simulations or the like, such that it exhibits high loss in biological tissue at the frequency of the microwave energy. Similarly, the geometry of the transmission line may ensure that much less power is lost when there is no tissue in the gap, but air instead. For example, the device may exhibit about 1 dB return loss, i.e. 80% of power reflected back to the generator, compared to 20% when there is tissue there. Thus, four times as much power can be delivered when tissue is present in the gap. Biological tissue is lossy, i.e. it is a good absorber of microwave energy.

Preferably, the pair of jaw elements define a long-nosed forceps, e.g. where the jaws have a gharial-like appearance. For example, the length of the jaw elements may be more than twice, preferably more than 2.5 times, their maximum width. In embodiments suitable for insertion through the instrument channel of an endoscope, the pair of jaw elements may have a length of 7 mm or more and a maximum width of 2.4 mm or less. In other embodiment, the pair of jaw elements may have a length of 10 mm or more, preferably 20 mm or more. In embodiments where the device is used laparoscopically or in open surgery, the width of the jaws may be more than 2.4 mm, e.g. 3 mm or more. The pair of jaw elements may have a curved outer surface, e.g. to provide the forceps with a substantially circular transverse cross-section in order to facilitate insertion through the instrument channel of the endoscope. The pair of jaw elements may taper away from the coaxial cable, i.e. narrow towards a distal end. This may assist the forceps to negotiate corners or curves in the instrument channel.

The pair of jaw elements may be a continuation of the coaxial cable. In other words, the coaxial cable may be connected to the pair of jaw elements at a first end thereof, and wherein the pair of jaw elements extend lengthwise away from the coaxial cable. As explained below, the pair of jaw element may be constrained to move with the coaxial cable, e.g. relative to some means for opening and closing the jaws. The coaxial cable may include a suitable bracket for securing it to the pair of jaw elements.

The pair of jaw elements may comprises a first jaw element and a second jaw element, the first jaw element having a first inner surface that opposes a second inner surface on the second jaw element across the gap, the first inner surface and the second inner surface extend lengthwise along their respective jaw elements. The first inner surface and the second inner surface may be shaped to meet along a contact surface when the jaws are closed. The first inner surface and the second inner surface may have cooperating (e.g. mating) shapes. Preferably they are flat.

The inner surfaces may have a thin oblong shape. If the jaw elements taper towards their distal ends, the inner surface may have a trapezoidal shape.

The pair of elongate conductive elements may comprise a first elongate conductive element mounted on the first inner surface and a second elongate conductive element mounted on the second inner surface. However, in a preferred embodiment, the pair of elongate conductive elements may comprise a first elongate conductive element mounted on the first inner surface and a second elongate conductive element mounted on the first inner surface, parallel to and separated from the first elongate conductive element. In this arrangement the spacing of the pair of elongate conductive members does not depend on the size of the gap between the jaw elements. The inner surface may thus deliver energy to tissue in contact therewith in a consistent manner.

In a preferred embodiment, both jaw elements have a pair of elongate conductive elements on their respective inner surfaces. Thus, the forceps may include a second pair of elongate conductive elements, the second pair of elongate conductive elements comprising a third elongate conductive element mounted on the second inner surface and a fourth elongate conductive element mounted on the second inner surface, parallel to and separated from the third elongate conductive element. This arrangement means that energy can be delivered from both jaw elements into tissue that is gripped in the gap. To achieve a consistent energy delivery profile, the third elongate conductive element and the fourth elongate conductive element may be positioned to mirror the first elongate conductive element and the second elongate conductive element across the gap. Preferably, the elongate conductive elements that face each other across the gap are of the same polarity.

The elongate conductive elements may comprise any suitably thin conductor. Materials with high conductivity may be desirable, e.g. silver, gold or stainless steel. For example, they may be wire or plated metal, e.g. having a width of 0.25 mm or less. The conductive elements may be straight. However, in one embodiment the elongate conductive elements may have a convoluted, e.g. meandering, distal portion. This structure may reduce the reflected signal (e.g. by effectively lengthening the conductive element). Moreover, by increasing the extent of the convolution towards the distal end, the amount of power lost over the area of the inner surface may be made more even because there is more transmission line in distal regions of low signal strength and less transmission line in proximal regions of high signal strength.

The forceps may include a spring arranged to urge the pair of jaw elements into an open configuration. In embodiments where the forceps are to be used at the distal end of an endoscope, the jaw closing mechanism is likely to be at the proximal end, whereby it is necessary to transmit the open-close force along the length of the endoscope. By providing a spring, e.g. a miniature torsion spring in the pivot joint or a sprung connectors between the elongate conductive elements and the coaxial cable, the force that needs to be transferred down the endoscope can be reduced.

The pair of jaw elements may comprise a first jaw element and a second jaw element that is rotatably secured to the first jaw element via a pivot joint located at a proximal end of the first jaw element and the second jaw element. The pivot joint may be integral to the pair of jaw elements. For example, the pivot joint may comprise cooperating engagement elements formed on the first jaw element and the second jaw element. The cooperating elements may be of the cup and boss type, where relative rotation (of the boss in the cup) is permitting, but separation of the cup and boss is restricted.

The pivot joint may include an aperture for receiving the coaxial cable, i.e. for allowing physical access to the inner surfaces of the pair of jaw elements. The aperture may be formed from recesses or cut outs in the pair of jaw elements, which mirror each other to form a passage through the jaw elements when there are interconnected.

The forceps may include a sleeve mounted over the coaxial cable and the pair of jaw elements, the sleeve being slidable relative to the pair of jaw elements to open and close the gap. The sleeve may have an internal diameter shaped to cause the jaw elements to close as it is drawn over them. Sliding the sleeve relative to the coaxial cable may be performed under the control of a jaw closing mechanism in a handle of the forceps. The jaw closing mechanism may act directly on the sleeve, or may include pull wires and push rods or the like. The sleeve may be rigid or flexible. In one embodiment the sleeve may comprise a laser-cut stainless steel tube.

In an alternative embodiment, the pivot joint may comprise a hinge pin secured to the coaxial cable, the first jaw element and the second jaw element being pivotably mounted on the hinge pin. In this arrangement, the jaws can be opened and closed by moving them relative to the coaxial cable. Thus the forceps may include a jaw closure member secured to the first jaw element and the second jaw element, the jaw closure member being movable relative to the coaxial cable. The jaw closure member may be a pull rod extending alongside the coaxial cable or a pull sleeve mounted around the coaxial cable.

To provide structural strength to each jaw element, the forceps may provide a reinforcing shell or casing on a proximal end of each of the pair of jaw elements. In a preferred embodiment, the reinforcing shell may perform a double function. Here, the reinforcing shell may be made from electrically conductive material, and may be electrically connected between an outer conductor of the coaxial cable and one of the pair of elongate conductive elements. The jaw element may thus be capable of transmitted a force, e.g. a physical pressure, on to the material gripped between the jaw elements. The pressure applied may be enough to close or partly close a gripped blood vessel before the application of RF or microwave energy in order to facilitate a vessel sealing procedure. This configuration for the jaw elements may also enable them to remain relatively cool throughout the treatment, which reduces the risk of tearing or rupturing the tissue during opening of the jaws after the vessel is sealed.

Herein, radiofrequency (RF) may mean a stable fixed frequency in the range 10 kHz to 300 MHz and the microwave energy may have a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

As mentioned above, the electrosurgical forceps of the invention may be configured for insertion down an instrument channel of an endoscope, or may be arranged for use in laparoscopic surgery or in a NOTES procedure or in a general open procedure.

The forceps may include a jaw closing mechanism in mechanical communication with the pair of jaw elements. For example, the jaw closing mechanism may include a handle and pull trigger in communication with the pair of jaw elements via one or more pull wires. In one implementation, the jaw closing mechanism may comprises a ratchet mechanism that permits the jaws to move between a plurality of preset separation positions. An advantage of this is to provide control over the pressure applied to the tissue grasped between the jaw elements. By fixing the position of the jaw elements, the pressure may be kept substantially constant during treatment. Moreover, the magnitude of the pressure applied may be related to the position of the ratchet, which may allow easily repeatable treatment configurations to be used.

The pair of jaw elements may be rotatable, e.g. by rotating the coaxial cable or sleeve. The device may include means for rotating the jaws in situ. For example, a handle may be mounted e.g. clipped, on the coaxial cable, e.g. at a proximal end thereof. Rotation of the coaxial cable using the handle may be transferred to the jaw elements. The handle may be integrated with an actuator (e.g. a slider or the like) for the jaw closing mechanism.

Other aspects of the invention may include a complete electrosurgical apparatus comprising the forceps described in communication with a jaw closure mechanism and an electrosurgical generator for delivering RF and/or microwave energy.

BRIEF DESCRIPTION OF THE DRAWINGS

Embodiments of the invention are discussed below in detail with reference to the accompanying drawings, in which.

DETAILED DESCRIPTION; FURTHER OPTIONS AND PREFERENCES

Figure 1:
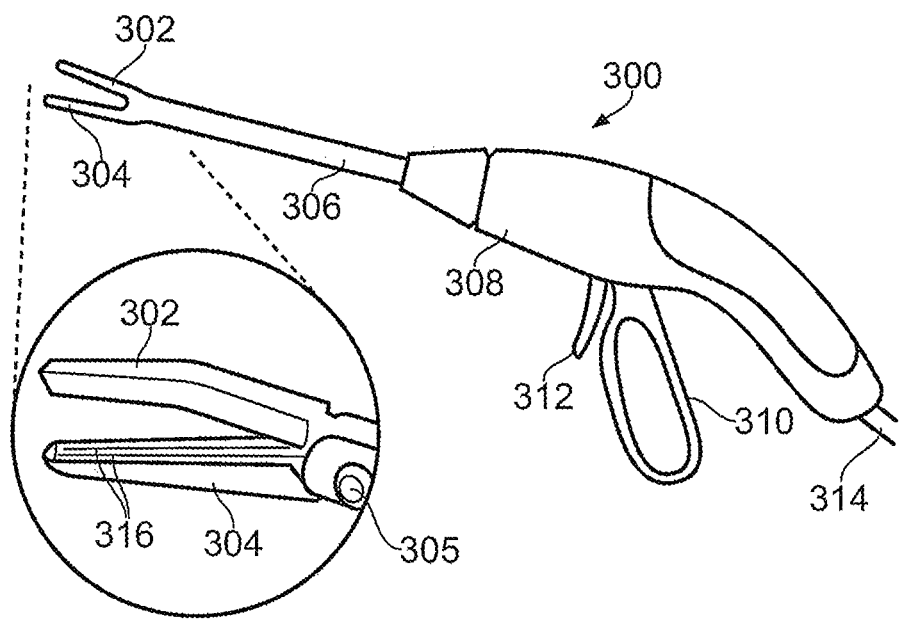
FIG. 1 is a schematic drawing of an electrosurgical forceps that is an embodiment of the invention.

The present invention provides an electrosurgical forceps structure that can be operated through the channel of an endoscope. The diameter of the channel in the endoscope may be 2.2 mm, 2.8 mm or 3.2 mm. The overall size of the forceps may be selected accordingly.

The present invention is particularly concerned with long thin-nosed forceps comprising a pair of jaw elements with a elongate, preferably tapering, shape. For example, the jaw element may have a length of 7 mm or more, e.g. 10 mm, and possibly 20 mm, and a maximum diameter of 2.4 mm. For endoscopic use, the length of the jaws may limit the ability of the device to be inserted along a convoluted endoscope channel. Thus, the longer length forceps may be used in other procedures, e.g. laparoscopies, or even open surgery.

The jaw elements of the electrosurgical forceps of the present invention have an electrode configuration that enables them to deliver radiofrequency (RF) or microwave energy into tissue that is gripped between them. The purpose of the forceps is to grasp (i.e. apply pressure to) the tissue and to cut, coagulate or cauterise the portion held between the forceps using the RF or microwave energy. Having longer forceps may allow longer sections of tissue to be grasped.

In order to effectively seal blood vessels, it is necessary to produce haemostasis in arteries, veins and tissue bundles. Microwave energy is effective for this purpose, as it can create a plug or region of coagulation to a controllable depth (related to the square of the electric field strength, which in turn is a function of the frequency of the microwave energy). A combination of RE and microwave energy may be used to create an effective seal. It is beneficial for the energy delivery to be combined with the application of pressure to the vessel, e.g. by clamping between a pair of jaw elements.

The combination of temperature elevation due to the use of RF and/or microwave energy and physical pressure may be particularly conducive to the process of shrinking and denaturing collagen and other cellular proteins in an irreversible manner. The structure of collagen changes as its bonds become broken, whereby it forms a gel-like substance that acts a glue between the vessel walls. In order to transform collagen in this way, the tissue needs to be heated between 70° C. and 95° C., which is sufficient to convert collagen and elastin in the tissue to gelatin. As the gelatin cools while under compression, it produces an effective seal across the lumen of the blood vessel. This seal may withstand the pressures associated with blood being pumped around the body. It follow from this analysis that it is desirable for the jaw element to remain clamped around the blood vessel after the RF and/or microwave energy have been applied to convert the collagen etc. to gelatin. When the fusion is complete, the vessel is plastically flexible at the seal.

One particular area of use envisaged for the invention is the removal of polyps, e.g. from the gastrointestinal tract, by cutting (and sealing) through the polyp's stalk. Having a longer nose may make the invention useful in removing polyps with wider, i.e. larger diameter, stalks.

In order to enable the device to deliver bipolar RF voltage and current as well as microwave energy, the electrode structures on the jaw elements of the forceps are transmission lines whose ends are arranged to be an open circuit.

Given that the device will need to deliver microwave and/or RF energy when the jaw elements are at different angles, the electrode structures are non designed to radiate microwave energy. This contrasts with conventional microwave forceps, which seek to provide a radiating antenna type arrangement. In the present invention, one or preferably both jaws of the forceps include unbalanced lossy transmission lines.

FIG. 1 shows a schematic view of an endoscopic microwave forceps 300 that is an embodiment of the invention. The forceps 300 comprises a body 308 having a flexible feed cable 306 extending from it. The feed cable 306 is not drawn to scale; it has a length and diameter suitable for insertion down the instrument channel of an endoscope (not shown). The cable may be less than 2.8 mm in overall diameter to allow it to be inserted down the instrument channel of an endoscope or a gastroscope. The cable may have a length of 2 m or more. The feed cable 306 comprises a outer sleeve that contains the coaxial cable and a jaw opening mechanism (discussed below). At a distal end of the cable 306 are a pair of jaw elements 302, 304, which are pivotable relative to each other about a hinge 305 to open and close a space between opposing surfaces thereof under the control of the jaw opening mechanism.

The body 308 includes a handle 310 and pull trigger 312 which operates the jaw closing mechanism. The pull trigger 312 may alternatively be a mechanical slider or any other suitable mechanism that allow the jaws to be opened and closed in order to apply pressure to material between the opposing surface of the jaw elements 302, 304. The body 308 is connected by a suitable cable 314 to an electrosurgical generator (not shown) capable of generating RF and microwave energy. A suitable generator for this purpose is described in WO 2012/076844, which is incorporated herein by reference. This generator is arranged to measure in real time delivered power on both a microwave channel and an RF channel (e.g. by comparing reflected microwave power to forward microwave power and by detecting RF voltage and current respectively). This information can be used to control an energy delivery profile in order to produce a good seal, since the heating lowers the water content within the vessel, which in turn reduces its ability to conduct electrical current. The change in composition of the vessel manifests itself as a change in impedance, which is detected in changes to the delivered power.

A pair of transmission lines 316 are formed on the inside surface of the lower jaw element 304. The transmission lines 316 may be made from wire (e.g. metal rods having a diameter of 0.25 mm or the like) or may be metal strip lines (e.g. having a width of 0.25 mm). In this embodiment, the transmission lines 316 run parallel to each other.

The end of each of the transmission lines 316 is an open circuit. In this embodiment one of the transmission lines 316 is connected to the inner conductor of the coaxial cable and the other is connector to the outer conductor. The transmission lines may thus operate as either active and return electrodes for an RF signal, or as a lossy transmission line for a microwave signal.

Figure 2:
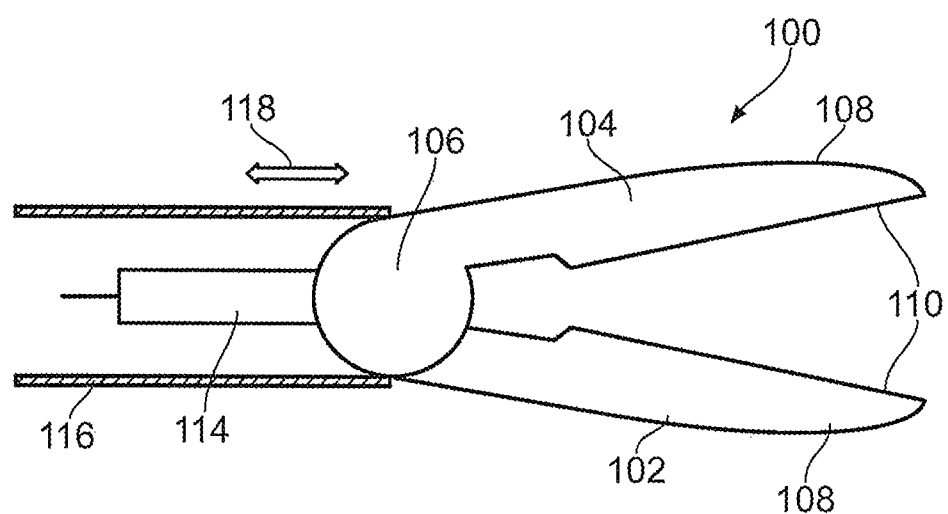
FIG. 2 is a schematic side view of an electrosurgical forceps that is an embodiment of the invention.

FIG. 2 shows a schematic view of an electrosurgical forceps 100 that is an embodiment of the invention. The forceps 100 comprises a pair of jaw elements 102, 104 which are pivotably connected to each other at a pivot joint 106 located at their proximal ends. Details of the pivot joint 106 are discussed below with reference to FIG. 3A. Each jaw element may comprise a body formed of a dielectric material with a low dielectric constant, such as quartz, ceramic (e.g. alumina), PEEK, PTFE, or the like. Having a low dielectric constant facilitate the propagation of the RF and microwave signals to the distal end of the jaw elements, even when they are gripping biological tissue.

Each jaw element 102, 104 has a length of about 20 mm and a width of less than 1.2 mm. Each jaw element 102, 104 has a smoothly curved outer surface 108 and an inner engagement surface 110. The inner engagement surfaces 110 oppose one another such that tissue can be gripped in between when in use. The inner engagement surfaces 110 are flat in this embodiment, but other surface profiles may be used.

One or both of the inner engagement surfaces 110 has an electrode configuration 112 (see FIG. 3B) attached or otherwise mounted thereon. The electrode configuration is exposed such that they will make contact with tissue in use. Further details of the electrode configurations that can be used in the present invention are discussed below with reference to FIGS. 4A to 4D.

Figures 3A, 3B:
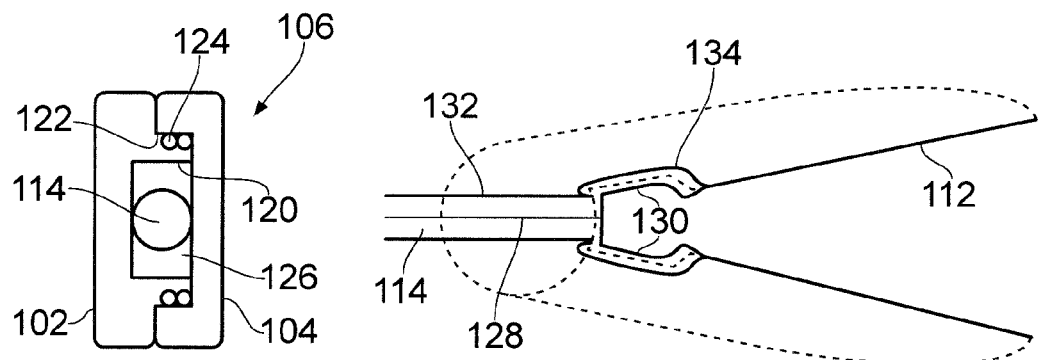
FIG. 3A is a transverse cross-sectional view through the electrosurgical forceps of FIG. 2.
FIG. 3B is a partial longitudinal cross-sectional view through the electrosurgical forceps of FIG. 2.

A coaxial cable 114 feeds into the proximal end of the pivot joint 106, as shown in FIG. 3A. Inside the pivot joint 106 an inner conductor and an outer conductor of the coaxial cable are connected to the electrode configuration 112 (see FIG. 3B).

The coaxial cable 114 and the forceps 100 are mounted in a sleeve 116. The sleeve 116 is slidable relative to the coaxial cable and forceps 100 in the direction of arrow 118 so that its can move over the proximal part of the forceps 100 to close the jaws. The coaxial cable may be secured to a rigid bracket (see FIG. 9) so that the pivot joint can transmit a compressing (push) force and a tensioning (pull) force on the forceps. The distal end of the coaxial cable may also be reinforced for this purpose. The coaxial cable 114 and sleeve 116 may in turn be connected to the relatively moving parts of the closing mechanism in the handle of the device. This connection may be via pull rods or may be direct.

FIG. 3A shows a cross-sectional view through the pivot joint 106. In this embodiment the pivot joint is a cup-boss type interface between cooperating formations on the jaw elements 102, 104. The first jaw element 102 has a projecting boss 120 which is receiving in a cooperating cup 122 formed in the second jaw element 104. The boss 120 may include a retaining flange (not shown) that snap fits into a corresponding groove in the cup 122 in order to secure the joint in an axial sense, whilst also permitting rotation.

Both the cup and the boss may include a circumferential cut out at the proximal side of the pivot joint. The cut outs cooperate to form an aperture 126 through the pivot joint 106, which can receive the distal end of the coaxial cable 114. Although not shown here, the coaxial cable 114 may be secured to the inner surfaces of the pivot joint 106 by a suitable bracket (not shown) that permits rotating movement of the jaw elements 102, 104 relative to the coaxial cable 114, but which transfers the forward and backward movement of the coaxial cable 114 relative to the sleeve 116.

A small torsion spring 124 may be mounted in the pivot joint 106. The torsion spring 124 may apply a torque that urges the jaw elements apart. The torque may be selected so that it is not strong enough to force the sleeve back along the coaxial cable, but rather assists the manual opening of the jaws.

FIG. 3B shows a schematic drawing of the electrical connections that are made at the distal end of the coaxial cable 114. The inner conductor 128 of the coaxial cable 114 is electrically connected to an electrode configuration 112 on the inner surface of each jaw element by a first conductive link element 130. The first conductive link element 130 may be a short flexible wire that enables the jaws to open whilst maintaining contact, or a metallised section of the jaw element. Alternatively, the conductive link may be a spring contact, which may also provides a biasing force that assists with opening the jaws.

Similarly, the outer conductor 132 of the coaxial cable 114 is electrically connected to the electrode configuration 112 on the inner surface of each jaw element by a second conductive link element 134. Again, the second conductive link element may be a short flexible wire or a metallised section of the jaw element. However, in an alternative arrangement, the outer surface of the proximal end of both jaw elements may be encased in a metal shell. The metal shell may act as the second conductive link element 134, i.e. extend round one side of the jaw element and terminate in a suitable electrode structure. In addition, the metal shell may improve the mechanical strength of the jaw elements 102, 104. This structure is discussed below with reference to FIG. 10.

Figures 4A, 4B:
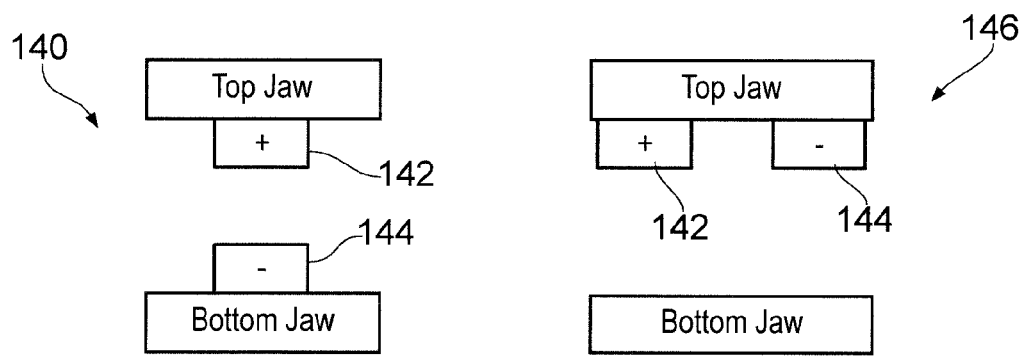
FIG. 4A is a first transmission line configuration for an electrosurgical forceps that is an embodiment of the invention.
FIG. 4B is a second transmission line configuration for an electrosurgical forceps that is an embodiment of the invention.

FIG. 4A shows a cross-sectional view of a first electrode (transmission line) configuration 140 for an electrosurgical forceps that is an embodiment of the invention. The first electrode configuration comprises two wire (or microstrip) transmission lines 142, 144, with one wire on each jaw. In this form, if the jaws are parallel, microwave transmission can take place along the length of the jaws. The tissue between the jaws becomes the dielectric of the transmission line, with nearly all the power travelling in the tissue between the jaws. The evenness of the heating will depend on the microwave properties of the tissue, i.e. relative permittivity and conductivity.

This configuration is less favoured because, for highly absorptive tissue or wide separation of the jaws, the microwave power may be nearly all absorbed near the feed end. If the jaws are not parallel, but are rather spread towards the tip, the heating will be even more concentrated near the feed end.

FIG. 4B shows a cross-sectional view of a second electrode (transmission line) configuration 146. The second electrode configuration 146 comprises two wire (or microstrip) transmission lines 142, 144 formed on the same jaw. In this form, the wires form a parallel wire transmission line. When the jaws are closed onto tissue, one half of the transmission line cross-section has tissue as its dielectric medium. Because of the high dielectric constant of the tissue, more than that proportion of the power will travel though the tissue, and heat the tissue close to the transmission line. Heating will take place preferentially close to the wires. The pattern of heating will be independent of how far the jaws are closed, which is advantageous when large diameter vessels (which cause the jaw elements to be non-parallel) are treated. Because some of the power travels outside the tissue, the heating can extend further along the jaws. If the absorption is low, some power will be reflected from the open circuit end of the transmission line and cause enhanced heating near the end, and in some cases, reduced heating a short distance from the end, due to interference between outgoing and reflected microwave energy.

The geometry of this configuration, especially the fixed wire separation that is independent of how far the jaws are closed, is suitable for delivering bipolar RF energy.

Figure 5A:
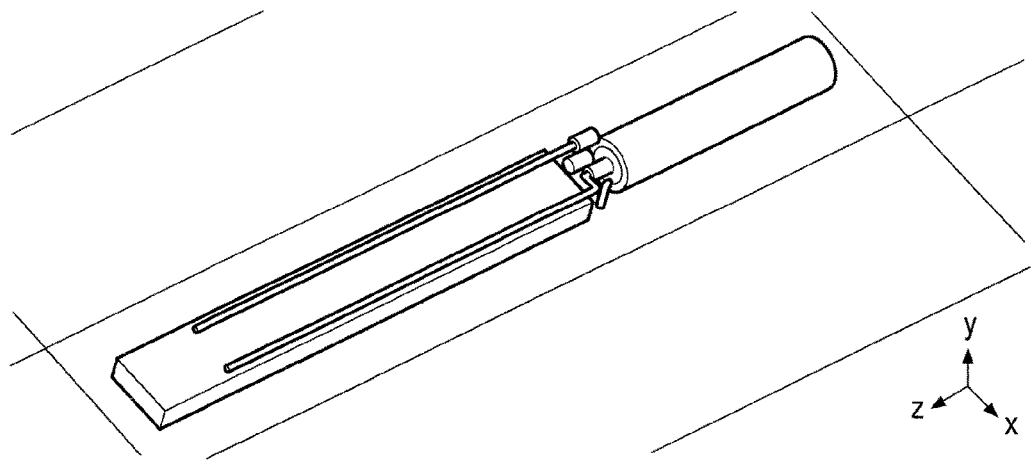
FIG. 5A is a perspective view of a modelled structure corresponding to the transmission line configuration of FIG. 4A.

An example of this geometry was simulated using CST Microwave Studio®, for a blood load 1 mm thick, with 0.25 mm diameter wires with their centres 2 mm apart. These were fed from modelled coaxial cable (based on a Sucoform 047 cable having an outer diameter of 1.2 mm) using the simple arrangement shown in FIG. 5A, which gave about a 5 dB return loss.

Figure 5B:
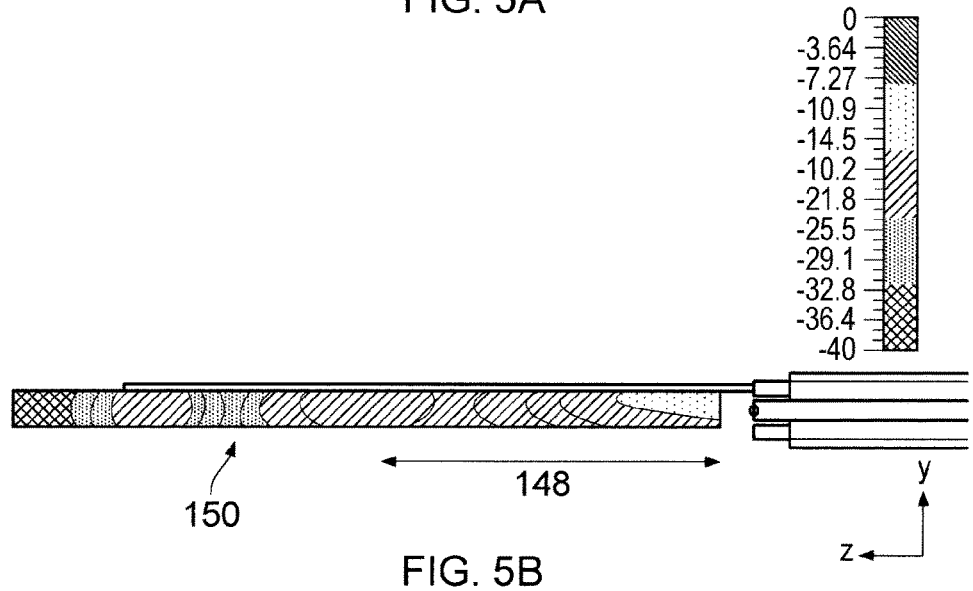
FIG. 5B is a side view of the modelled structure of FIG. 5A showing simulated power loss density in blood.
Figure 5C:
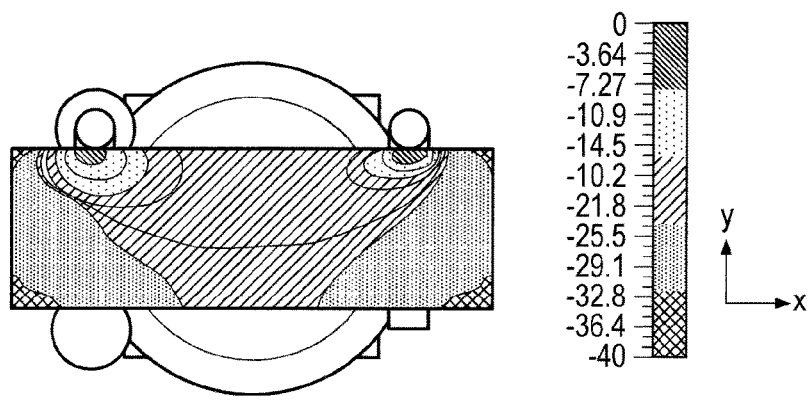
FIG. 5C is a transverse cross-sectional view of the modelled structure of FIG. 5A showing simulated power loss density in blood.

The longitudinal heating calculated by this simulation can be seen in FIG. 5B. The heating is fairly constant in a proximal half 148 of the electrode configuration, but towards the distal end the heating reduces and there is a null 150 caused by destructive interference due to reflection from the end.

The cross-sectional view of the simulation shown in FIG. illustrates that the heating extends across the full depth of the blood, although there is the more intense heating directly under each line and the overall transverse profile describes a curve.

Figures 4C, 4D:
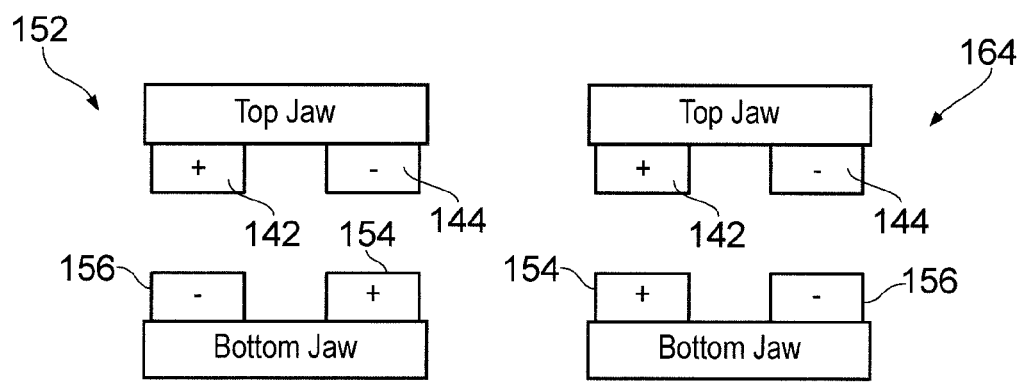
FIG. 4C is a third transmission line configuration for an electrosurgical forceps that is an embodiment of the invention.
FIG. 4D is a fourth transmission line configuration for an electrosurgical forceps that is an embodiment of the invention.

FIG. 4C shows a cross-sectional view of a third electrode (transmission line) configuration 152. The third electrode configuration 152 comprises four wire transmission lines 142, 144, 154, 156, two on each jaw, with opposite polarities facing each other on the other jaw.

In this form, each jaw will behave as in shown in FIG. 4B when the jaws are far apart. There will thus be heating on both sides of the tissue, which may be advantageous. However, when the jaws are close together there may be more microwave power and more heating in the region between the jaws than when they are open due to the presence of the opposite polarity wire in the other jaw. Because of this, the heating may be more concentrated near the feed end, particularly as at this end the jaws will be closest together in most scenarios.

The third electrode (transmission line) configuration 152 is suitable for use with bipolar RF for the same reasons as the second configuration. However, when the jaws are close together there may be an additional path for the RF current between the jaws, which may be undesirable.

Figure 6A:
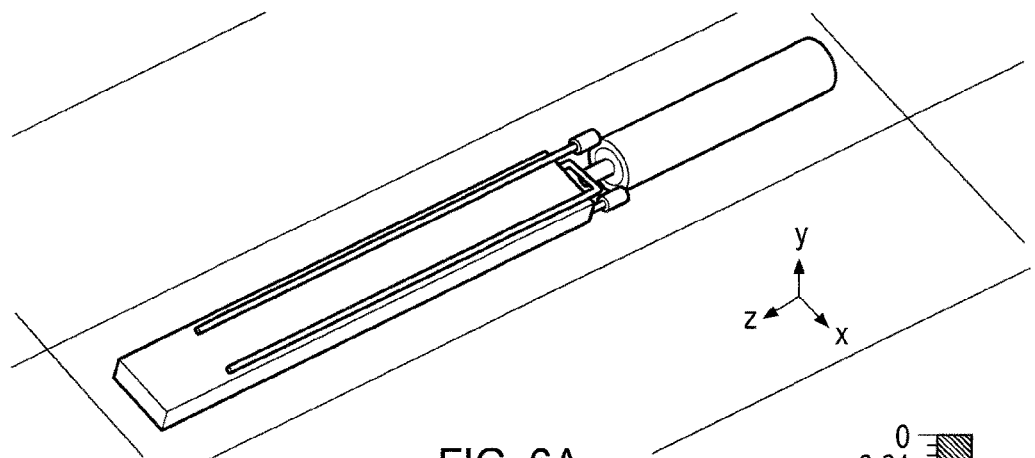
FIG. 6A is a perspective view of a modelled structure corresponding to the transmission line configuration of FIG. 4C.

An example of this geometry was simulated using CST Microwave Studio®, for a blood load 1 mm thick, with 0.25 mm diameter wires with their centres 2 mm apart (i.e. 1.75 mm between the outer edges of the wires). These were fed from modelled coaxial cable (based on a Sucoform 047 cable having an outer diameter of 1.2 mm) using the simple arrangement shown in FIG. 6A, which gave about a 5 dB return loss.

Figure 6B:
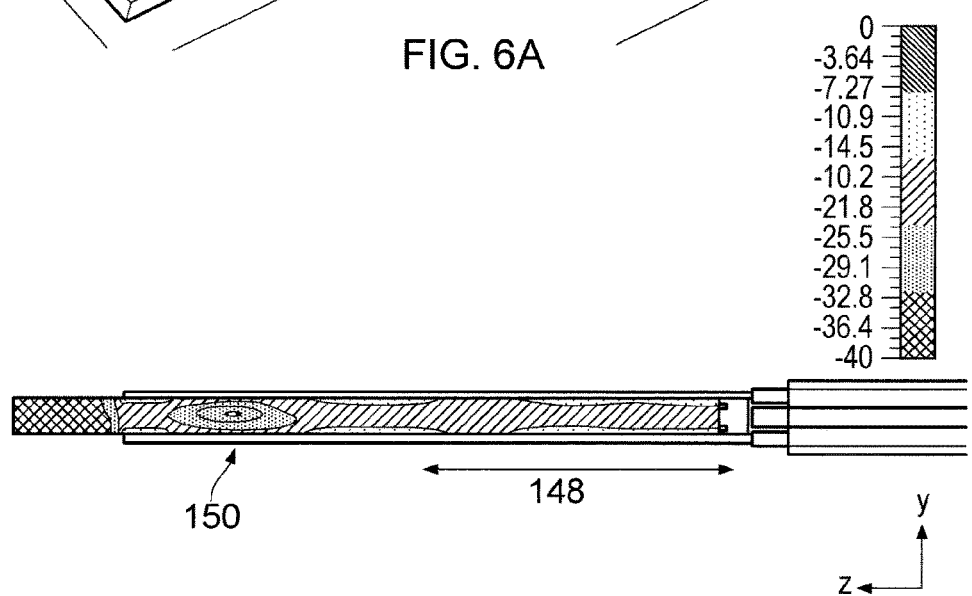
FIG. 6B is a side view of the modelled structure of FIG. 6A showing simulated power loss density in blood.

The longitudinal heating calculated by this simulation can be seen in FIG. 6B. Similarly to FIG. 5B the heating is fairly constant for the proximal half 148 of the electrode configuration. However, towards the distal end the heating reduces and there is a null 150 caused by destructive interference due to reflection from the end.

Figure 6C:
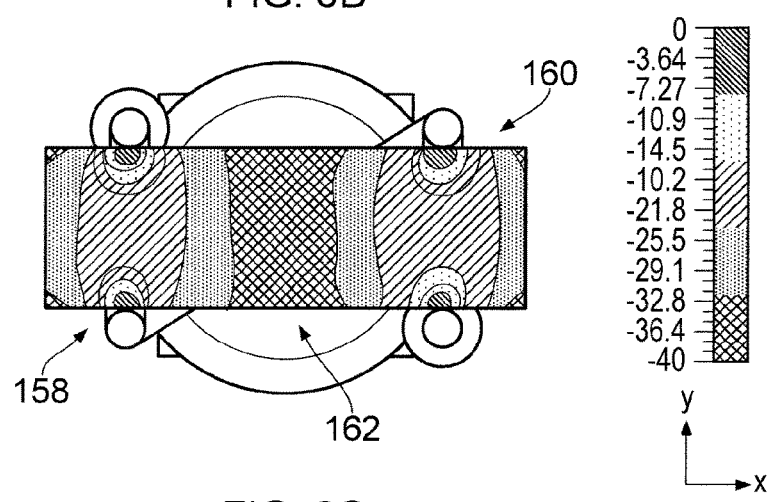
FIG. 6C is a transverse cross-sectional view of the modelled structure of FIG. 6A showing simulated power loss density in blood.

The heating profile across the full depth of the blood is shown in FIG. 6C. There are two bands of heating 158, 160 between the opposite jaws, with a cool gap 162 between. Heating is mainly between wires on opposite jaws, not between wires on the same jaw.

FIG. 4D shows a cross-sectional view of a fourth (and most preferred) electrode (transmission line) configuration 164. The fourth electrode configuration 164 comprises four wire transmission lines 142, 144, 154, 156, two on each jaw, with same polarities facing each other on the other jaw.

In this form, each jaw will behave as shown in FIG. 4B when the jaws are far apart and when the jaws are close together. Heating will be from both jaws.

The fourth electrode (transmission line) configuration 152 is suitable for use with bipolar RF for the same reasons as the second configuration. When the jaws are close together the paths for RF current remain similar, which ensures consistent behaviour while the jaws are in the process of being closed.

Figure 7A:
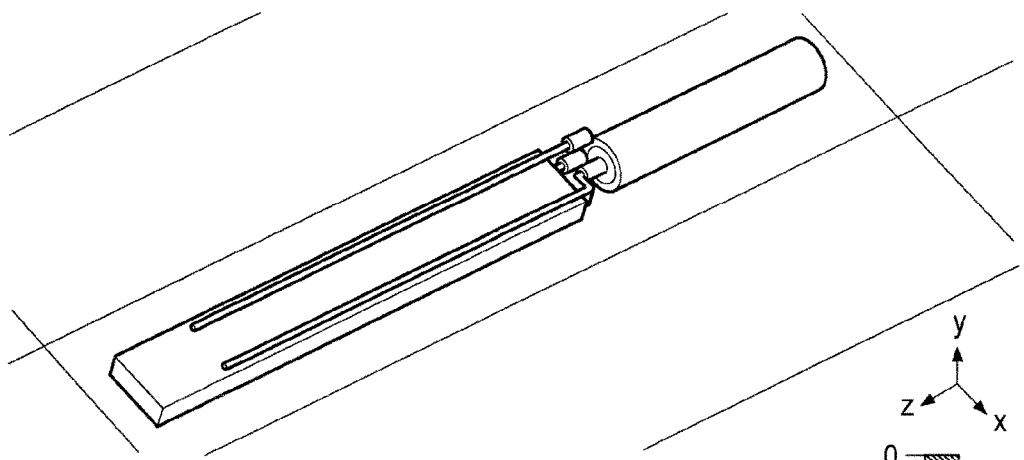
FIG. 7A is a perspective view of a modelled structure corresponding to the transmission line configuration of FIG. 4D.

An example of this geometry was simulated using CST Microwave Studio®, for a blood load 1 mm thick, with 0.25 mm diameter wires with their centres 2 mm apart (i.e. a physical separation of 1.75 mm between the conductors). These were fed from modelled coaxial cable (based on a Sucoform 047 cable having an outer diameter of 1.2 mm) using the simple arrangement shown in FIG. 7A, which gave about a 5 dB return loss.

Figure 7B:
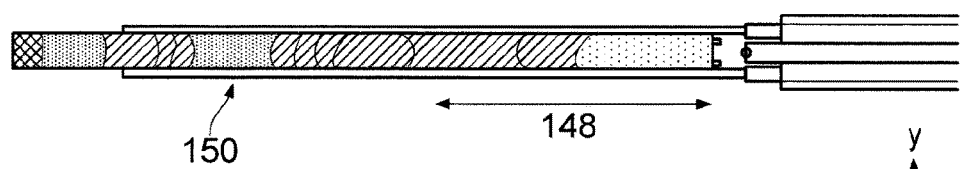
FIG. 7B is a side view of the modelled structure of FIG. 7A showing simulated power loss density in blood.
Figure 7B:

The longitudinal heating calculated by this simulation can be seen in FIG. 7B. Similarly to FIG. 5B the heating is fairly constant for the proximal half 148 of the electrode configuration. Towards the end distal the heating reduces and there is a null 150 caused by destructive interference due to reflection from the end.

Figure 7C:
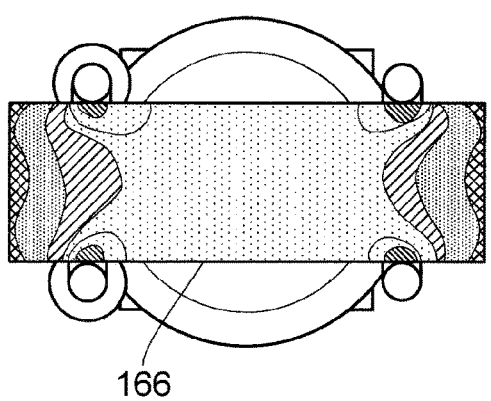
FIG. 7C is a transverse cross-sectional view of the modelled structure of FIG. 7A showing simulated power loss density in blood.
Figure 7C:
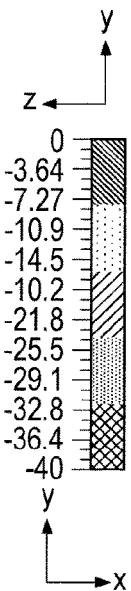

The heating profile across the full depth of the blood is shown in FIG. 7C. There is one wide band 166 of heating, between the four wires.

Figure 8A:
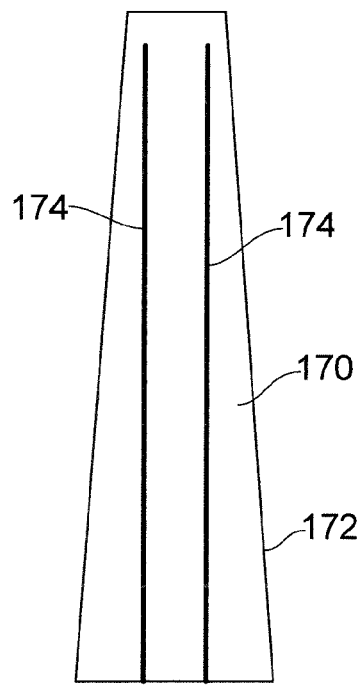
FIG. 8A is a schematic plan view of a first electrode arrangement for an electrosurgical forceps that is an embodiment of the invention.
Figure 8B:
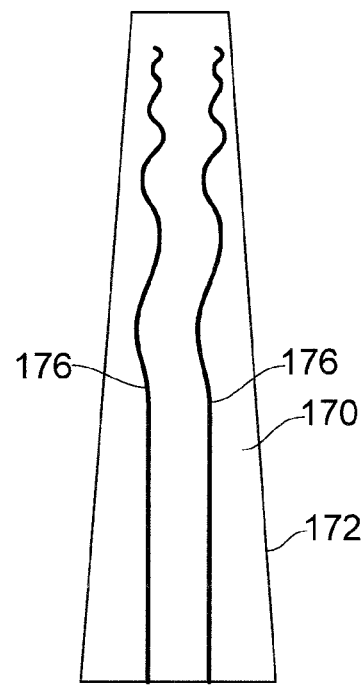
FIG. 8B is a schematic plan view of a second electrode arrangement for an electrosurgical forceps that is an embodiment of the invention.

FIG. 8A shows a plan view of an inner surface 170 of a jaw element 172. A pair of conductive strips 174, e.g. made of wire or a deposited strip of metal, provide the electrode configuration mentioned above. The conductive strips 174 are straight and parallel. As mentioned above, one side effect of this arrangement is a null in the delivered microwave energy at around three quarters of the way toward the distal end of the jaw element 172. FIG. 8B shows a plan view of an inner surface 170 of a jaw element 172 in which a pair of parallel conductive strips 176 have a distal portion that is convoluted instead of straight in order to reduce or minimize the null effect. The convoluted path effectively increases the length of the transmission lines in a manner that reduces the reflections from the distal end and therefore reduces the magnitude of the null.

Figure 9:
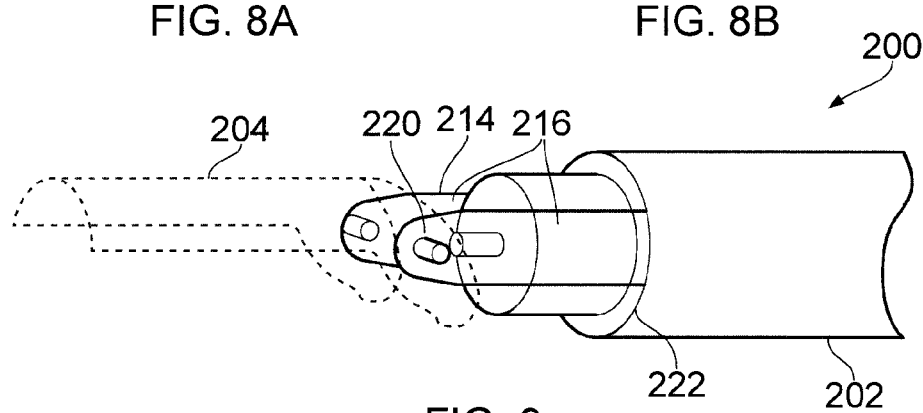
FIG. 9 is a schematic partial side view of an electrosurgical forceps that is another embodiment of the invention.

FIG. 9 is a schematic drawing showing a view of connection interface between a coaxial cable and jaw element in an electrosurgical forceps 200 that is another embodiment of the invention. In this embodiment, the jaw element is a three piece construction comprises a metal shell 204, a support body 206, e.g. of rigid plastic, and a dielectric base 208, e.g. of ceramic, for supporting the active electrode. The lower jaw element and the support body and dielectric base of the upper jaw element are omitted from FIG. 9 for clarity. In another embodiment, the jaw element may be formed from a stainless steel body, with portions of gold metallisation formed thereon to provide the first and second conductive elements. In this arrangement, the jaw elements may be electrically isolated from each other by formed the pivot mechanism from an insulating material such as ceramic. For example, if a hinge is used, the hinge pin may be formed from ceramic and one or more ceramic shims may be located between surfaces of the jaws that may slide past one another.

Figure 10:
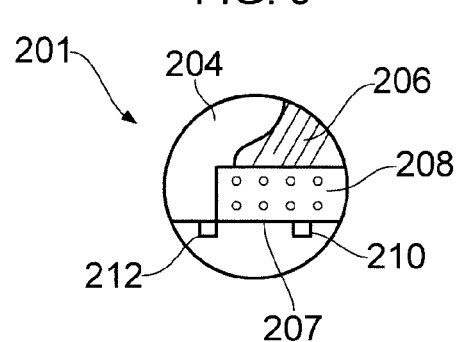
FIG. 10 is a cross-sectional view through a jaw element that can be used in an electrosurgical forceps that is another embodiment of the invention.

FIG. 10 shows a cross-sectional view through the three pieces of the jaw element 201. It can be seen that the inner surface 207 of the jaw element 201 has two conductive wires 210, 212. The first conductive wire 210 is mounted on the dielectric base 208, which isolates it from the second conductive wire 212 and supports propagation of RF and microwave energy. The second conductive wire 212 is part of the metal shell 204. The support body 206 is effectively an electrically insulating fill between the metal shell 204 and the dielectric base 208. The outer surfaces of the metal shell 204 and support body 206 are shaped to give the jaw element a smooth outward appearance.

Each jaw element has its own respective metal shell 204. The metal shells 204 are pivotable relative to each other about a hinge element 214. The hinge element 214 comprises a pair of hinge bars 216 secured to the distal end of the coaxial cable 202, and a pair of inwardly projecting stubs which mate with corresponding slots 220 on the metal shells 204. In use, the coaxial cable may be pulled or pushed relative to a surrounding sleeve (not shown) to cause the metal shells 204 to pivot about the hinge and thereby open and The hinge element 214 may be made of conductive material, and may also act as a conductive link between the outer conductor 222 of the coaxial cable 202 and the metal shell 204. The inner conductor 224 of the coaxial cable 202 may be connected to the first conductive wire 210 by a separately conductive link element (not shown), such as a short flexible wire made of silver, gold or any other highly conductive material.

Figure 11:
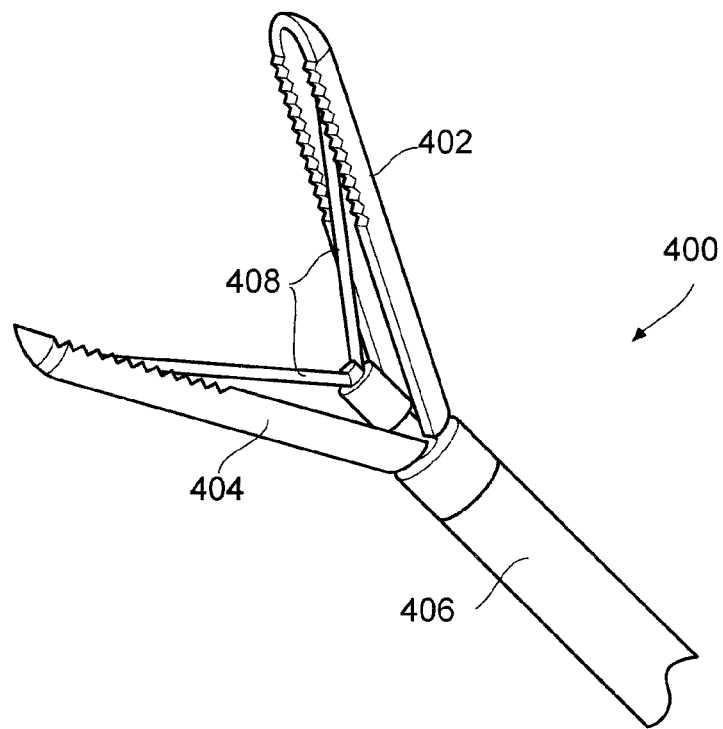
FIG. 11 is a schematic perspective view of an electrosurgical forceps that is an embodiment of the invention.

FIG. 11 shows a schematic view of one example of a jaw configuration that could be used in an electrosurgical forceps 400 that is an embodiment of the invention. The forceps 400 comprise a pair of jaw elements 402, 404 hinged to the distal end of a sleeve 406. The sleeve 406 carries a coaxial cable (not shown) for conveying RF and/or microwave energy to the jaw elements, and a jaw opening mechanism. In this embodiment, the jaw opening mechanism comprises a pair of flexible push rods 408 that extend through the sleeve and protrude at the distal end. Each push rod is attached to the underside of a respective jaw element. The jaw elements 402, 404 may thus be opened and closed by extending and retracting the push rods 408.

Figure 12:
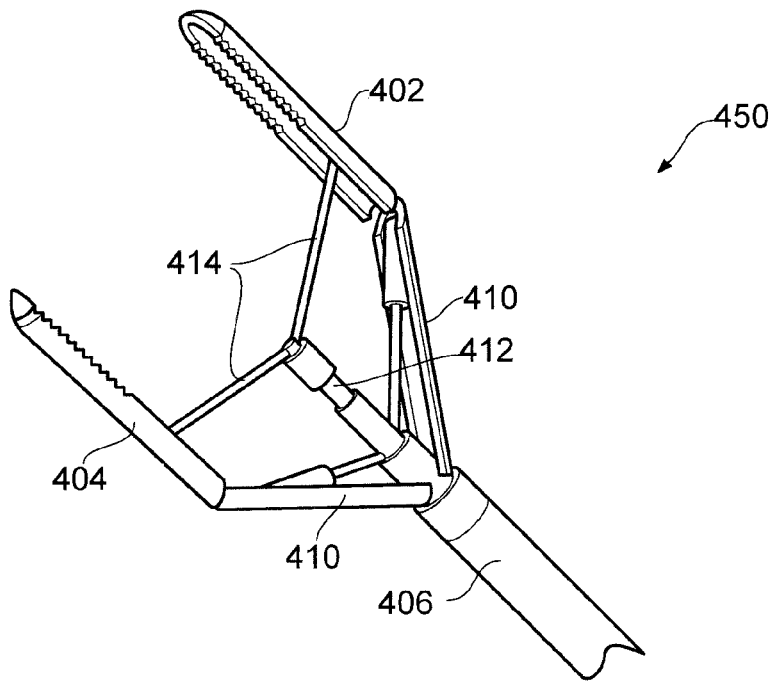
FIG. 12 is a schematic perspective view of another electrosurgical forceps that is an embodiment of the invention.

FIG. 12 shows a schematic view of a pantograph-type jaw configuration that could be used in an electrosurgical forceps 450 that is an embodiment of the invention. The forceps 450 comprise a pair of jaw elements 402, 404, which are each pivotably mounted on a extension element 410, which in turn is hinged on the distal end of a sleeve 406. The sleeve 406 carries a coaxial cable (not shown) for conveying RF and/or microwave energy to the jaw elements, and a jaw opening mechanism. In this embodiment, the jaw opening mechanism comprises a push rod 412 that extends through the sleeve and protrudes at its distal end. The push rod 412 has a pair of rigid, fixed length connector rods 414 pivotably attached at its distal end. Each connector rod 414 is attached to the underside of a respective jaw element. The jaw elements 402, 404 may thus be opened and closed by extending and retracting the push rod 412, which causes the connector rods to force apart the jaw elements 402, 404.

In the embodiment shown in FIG. 12, the jaw elements may remain substantially parallel during opening and closing.

The forceps may be used in a method of vessel sealing that comprises three stages:

(1) applying pressure to the vessel (e.g. polyp stalk) by clamping it between the jaw elements to bring opposing side walls of the vessel closer to one another, (2) applying RF energy and/or microwave energy to the compressed tissue in order to heat the collagen therein and make it mobile through denaturation, (3) allow the collagen to cool while maintaining the pressure to seal the vessel.

The invention claimed is:

1. Electrosurgical forceps comprising:
   a pair of jaw elements that are pivotable relative to each other to open and close a gap therebetween, the pair of jaw elements comprising a first jaw element and a second jaw element that is rotatably secured to the first jaw element via a pivot joint located at a proximal end of the first jaw element and the second jaw element;
   a pair of elongate conductive elements, wherein each jaw element has a respective one of the pair of elongate conductive elements mounted therein adjacent to the gap; and
   a coaxial cable for conveying radiofrequency (RF) energy and/or microwave energy, wherein the pivot joint includes an aperture for receiving the coaxial cable, and wherein the pair of elongate conductive elements are electrically connected to the coaxial cable and arranged to act as both
      (i) an active electrode and a return electrode for RF energy conveyed by the coaxial cable, and
      (ii) a non-uniform unbalanced lossy transmission line to support the microwave energy as a travelling wave, the non-uniform unbalanced lossy transmission line being non-resonant for the microwave energy along the travelling wave.

2. Electrosurgical forceps according to claim 1, wherein the pair of jaw elements have a length of 5 mm or more and a maximum width of 2.4 mm or less.

3. Electrosurgical forceps according to claim 1, wherein the pair of jaw elements have a curved outer surface that tapers away from the coaxial cable.

4. Electrosurgical forceps according to claim 1, wherein the coaxial cable is connected to the pair of jaw elements at a first end thereof, and wherein the pair of jaw elements extend lengthwise away from the coaxial cable.

5. Electrosurgical forceps according to claim 4, wherein the first jaw element has a first inner surface that opposes a second inner surface on the second jaw element across the gap, the first inner surface and the second inner surface extending lengthwise along their respective jaw elements.

6. Electrosurgical forceps according to claim 5, wherein a first elongate conductive element of the pair of elongate conductive elements is mounted on the first inner surface and a second elongate conductive element of the pair of elongate conductive elements is mounted on the second inner surface.

7. Electrosurgical forceps according to claim 1, wherein the elongate conductive elements comprise wire or plated metal having a width of 0.25 mm or less.

8. Electrosurgical forceps according to claim 1 including a spring arranged to urge the pair of jaw elements into an open configuration.

9. Electrosurgical forceps according to claim 1, wherein the pivot joint comprises cooperating engagement elements formed on the first jaw element and the second jaw element.

10. Electrosurgical forceps according to claim 1 including a sleeve mounted over the coaxial cable and the pair of jaw elements, the sleeve being slidable relative to the pair of jaw elements to open and close the gap.

11. Electrosurgical forceps according to claim 1, wherein the pivot joint comprises a hinge pin secured to the coaxial cable, the first jaw element and the second jaw element being pivotably mounted on the hinge pin.

12. Electrosurgical forceps according to claim 11 including a jaw closure member secured to the first jaw element and the second jaw element, the jaw closure member being movable relative to the coaxial cable.

13. Electrosurgical forceps according to claim 12, wherein the jaw closure member is a pull rod extending alongside the coaxial cable or a pull sleeve mounted around the coaxial cable.

14. Electrosurgical forceps according to claim 12 including a ratchet mechanism connected to the jaw closure member to permit relative movement of the jaw elements between a plurality of preset separation positions.

15. Electrosurgical forceps according to claim 1, wherein the elongate conductive elements have a convoluted distal portion.

16. Electrosurgical forceps according to claim 1, wherein each jaw element in the pair of jaw elements has a reinforcing shell at its proximal end.

17. Electrosurgical forceps according to claim 16, wherein the reinforcing shell is made from electrically conductive material, and is electrically connected between an outer conductor of the coaxial cable and one of the pair of elongate conductive elements.

18. Electrosurgical forceps according to claim 16, wherein the jaw elements are configured to transmit a compression force to tissue grasped therebetween.

19. Electrosurgical forceps comprising:
a pair of jaw elements that are pivotable relative to each other to open and close a gap therebetween, the pair of jaw elements comprising a first jaw element and a second jaw element that is rotatably secured to the first jaw element via a pivot joint located at a proximal end of the first jaw element and the second jaw element, wherein the first jaw element has a first inner surface that opposes a second inner surface on the second jaw element across the gap, the first inner surface and the second inner surface extending lengthwise along their respective jaw elements;
a pair of elongate conductive elements, wherein the pair of elongate conductive elements comprises a first elongate conductive element mounted on the first inner surface and a-second elongate conductive element mounted on the first inner surface, parallel to and separated from the first elongate conductive element; and
a coaxial cable for conveying radiofrequency (RF) energy and/or microwave energy,
wherein the pivot joint includes an aperture for receiving the coaxial cable, and
wherein the pair of elongate conductive elements are electrically connected to the coaxial cable and arranged to act as both
(i) an active electrode and a return electrode for RF energy conveyed by the coaxial cable, and
(ii) a non-uniform unbalanced lossy transmission line to support the microwave energy as a travelling wave, the non-uniform unbalanced lossy transmission line being non-resonant for the microwave energy along the travelling wave.

20. Electrosurgical forceps according to claim 19 including a second pair of elongate conductive elements, the second pair of elongate conductive elements comprising a third elongate conductive element mounted on the second inner surface and a fourth elongate conductive element mounted on the second inner surface, parallel to and separated from the third elongate conductive element.

21. Electrosurgical forceps according to claim 20, wherein the third elongate conductive element and the fourth elongate conductive element are positioned to mirror the first elongate conductive element and the second elongate conductive element.

22. Electrosurgical forceps according to claim 21, wherein the elongate conductive elements that face each other across the gap are of opposite polarities.

23. Electrosurgical forceps according to claim 21, wherein the elongate conductive elements that face each other across the gap are of the same polarity, and wherein the elongate conductive elements located on the same inner surface are of opposite polarity.

* * * * *